United States Patent
Gillis

(10) Patent No.: US 11,442,068 B2
(45) Date of Patent: Sep. 13, 2022

(54) METHOD FOR DIAGNOSING AND TREATING FIBROMYALGIA

(71) Applicant: EPICGENETICS, INC., Los Angeles, CA (US)

(72) Inventor: Bruce S. Gillis, Beverly Hills, CA (US)

(73) Assignee: EPICGENETICS, INC., Los Angeles, CA (US)

(*) Notice: Subject to any disclaimer, the term of this patent is extended or adjusted under 35 U.S.C. 154(b) by 684 days.

(21) Appl. No.: 16/002,689

(22) Filed: Jun. 7, 2018

(65) Prior Publication Data

US 2018/0348233 A1 Dec. 6, 2018

Related U.S. Application Data

(63) Continuation of application No. 14/692,338, filed on Apr. 21, 2015, now Pat. No. 10,018,636, which is a continuation of application No. 14/444,779, filed on Jul. 28, 2014, now abandoned, which is a continuation of application No. 14/358,396, filed as application No. PCT/US2011/055985 on Oct. 12, 2011, now abandoned.

(60) Provisional application No. 61/392,371, filed on Oct. 12, 2010.

(51) Int. Cl.
*G01N 33/68* (2006.01)

(52) U.S. Cl.
CPC ..... *G01N 33/6863* (2013.01); *G01N 33/6866* (2013.01); *G01N 33/6869* (2013.01); *G01N 2333/523* (2013.01); *G01N 2333/5409* (2013.01); *G01N 2333/5412* (2013.01); *G01N 2333/5421* (2013.01); *G01N 2333/5428* (2013.01); *G01N 2333/57* (2013.01); *G01N 2800/10* (2013.01); *G01N 2800/2842* (2013.01); *G01N 2800/50* (2013.01); *G01N 2800/52* (2013.01); *G01N 2800/60* (2013.01); *G01N 2800/7095* (2013.01)

(58) Field of Classification Search
CPC .................................................. G01N 33/6863
See application file for complete search history.

(56) References Cited

U.S. PATENT DOCUMENTS

| | | |
|---|---|---|
| 10,018,636 B2 | 7/2018 | Gillis |
| 2006/0094056 A1 | 5/2006 | Chappell et al. |
| 2007/0197900 A1 | 8/2007 | Baudenbacher et al. |
| 2009/0234202 A1 | 9/2009 | Goix et al. |
| 2009/0280177 A1 | 11/2009 | Nishioka |
| 2014/0336076 A1 | 11/2014 | Gillis |
| 2015/0301062 A1 | 10/2015 | Gillis |

OTHER PUBLICATIONS

Ang, D.C., et al. MCP-1 and IL-8 as pain biomarkers in fibromyalgia: a pilot study. Pain Medicine, 2011, 12:1154-1161.*
Alonso et al., "Cytokine Patterns in Adults with AIDS," Immunological Investigations 26(3):341-350 (1997).
Bazzichi et al., "Cytokine patterns in fibromyalgia and their correlation with clinical manifestations," Clin. Exp. Rheum. 25:225-230 (2007).
Clauw, "Fibromyalgia. A Clinical Review," JAMA 311(15): 1547-1555 (2014).
Feng et al., "Missense Mutations in the MEFV Gene Are Associated with Fibromyalgia Syndrome and Correlate with Elevated IL-1β Plasma Levels," PLos One 4:e8480, 9 pages (2009).
Gur et al., "Regional cerebral blood flow and cytokines in young females with fibromyalgia," Clin. Exp. Rheumatol. 20:753-760 (2002).
Gur et al., "Cytokines and Depression in Cases with Fibromyalgia," J. Rheumatol. 29:358-361 (2002).
International Search Report, PCT appl. No. PCT/US2011/055985, 2 pages (dated Feb. 17, 2012).
Jason and Larned, "Single-cell cytokine profiles in normal humans: comparison of flow cytometric reagents and stimulation protocols," J. Immunol. Methods 207:13-22 (1997).
Kurtzhals et al., "Interleukin-4 and Interferon-Gamma Production by Leishmania Stimulated Peripheral Blood Mononuclear Cells from Nonexposed Individuals," Scand. J. Immunol. 41:343-349 (1995).
Leavitt et al., "Biological and Biochemical Properties of Phaseolus vulgaris Isolectins," J. Biol. Chem. 252(9):2961-2966 (1977).
Menzies and Lyon, "Integrated Review of the Association of Cytokines With Fibromyalgia and Fibromyalgia Core Symptoms," Biol. Research for Nursing 11:387-394 (2010).
Middleton et al., "The Prevalence and Clinical Impact of Fibromyalgia in Systemic Lupus Erythematosus," Arthritis & Rheumatism 37:1181-1188 (1994).
Morand et al., "Fibromyalgia Syndrome and Disease Activity in Systemic Lupus Erythematosus," Lupus 3:187-191 (1994).
Tishler et al., "Sleep disturbances, fibromyalgia and primary Sjögren's syndrome," Clin. Exp. Rheumatol. 15:71-74(1997).
Togo et al., "Plasma Cytokine Fluctuations over Time in Healthy Controls and Patients with Fibromyalgia," Exp. Biol. Med. 234:232-240 (2009).
Tsuchida and Sakane, "Intracellular Activation Signal Requirements for the Induction of IL-2 Responsiveness in Resting T Cell Subsets in Humans," J. Immunol. 140:3446-3449 (1988).
Vitali et al., "Fibromyalgia Features in Patients with Primary Sjogren's Syndrome," Scand. J. Rheumatol. 18:21-27 (1989).
Wallace et al., "Cytokines and immune regulation in patients with fibrositis," Arthritis & Rheumatism 32:1334-135 (1989).
Wallace et al., "Cytokines play an aetiopathogenetic role in fibromyalgia: a hypothesis and pilot study," Rheumatology 40:743-749 (2001).
Wang et al., "Circulating Cytokine Levels Compared to Pain in Patients with Fibromyalgia—A Prospective Longitudinal Study Over 6 Months," J. Rheumatol. 35:1366-1370 (2008).

(Continued)

*Primary Examiner* — Prema M Mertz
(74) *Attorney, Agent, or Firm* — Cooley LLP

(57) ABSTRACT

The invention provides methods, kits and reagents for diagnosing fibromyalgia (FM) in an individual by determining whether the levels of one or more cytokines in the individual are altered, as compared to control levels. The altered level(s) or patterns of expression of the cytokines measured in the affected individual compared to the level from the control is predictive/indicative of FM in the individual.

17 Claims, 1 Drawing Sheet

(56) References Cited

OTHER PUBLICATIONS

Wang et al., "The Role of IL-8 in Patients with Fibromyalgia. A Prospective Longitudinal Study of 6 Months," Clin. J. Pain. 25:1-4 (2009).
Wolfe and Michaud, "Severe Rheumatoid Arthritis (RA), Worse Outcomes, Comorbid Illness, and Sociodemographic Disadvantage Characterize RA Patients with Fibromyalgia," J. Rheumatol 31:695-700 (2004).
Written Opinion of the International Searching Authority, PCT appl. No. PCT/US2011/055985, 4 pages (dated Feb. 17, 2012).
Yachnin and Svenson, "The Immunological and Physicochemicla Properties of Mitogenic Proteins Derived from Phaseolus vulgaris," Immunol. 22:871-883 (1972).
BD™ Cytometric Bead Array (CBA) Human Th1/TH2 Cytokine Kit II, Instruction Manual. Downloaded Nov. 11, 2016.
Franke, A. et al. Postoperative PMBC-derived IL-6 and TNF-alpha-release is uninfluenced by IL-12-mediated restoration of IFN-gamma synthesis. Scandinavian Cardiovascular Journal. 2009, vol. 43, p. 136-144.
Cymbalta Summary Review for Regulatory Action, dated Jun. 13, 2008, 17 pages.
Arnold et al., "Gabapentin in the Treatment of Fibromyalgia A Randomized, Double-Blind, Placebo-Controlled, Multicenter Trial," Arthritis & Rheumatism 56(4):136-1344 (2007).
FDA Press Release, FDA Approves First Drug for Treating Fibromyalgia, dated Jun. 21, 2007, Retrieved Jan. 4, 2021 from the Internet at https://www.fda.gov/bbs/topics/NEWS/2007/new01656.html, 2 pages.
Mease et al., The Efficacy and Safety of Milnacipran for Treatment of Fibromyalgia. A Randomized, Double-blind, Placebo-controlled Trial, The Journal of Rheumatology 2009 36(2):398-409.

\* cited by examiner

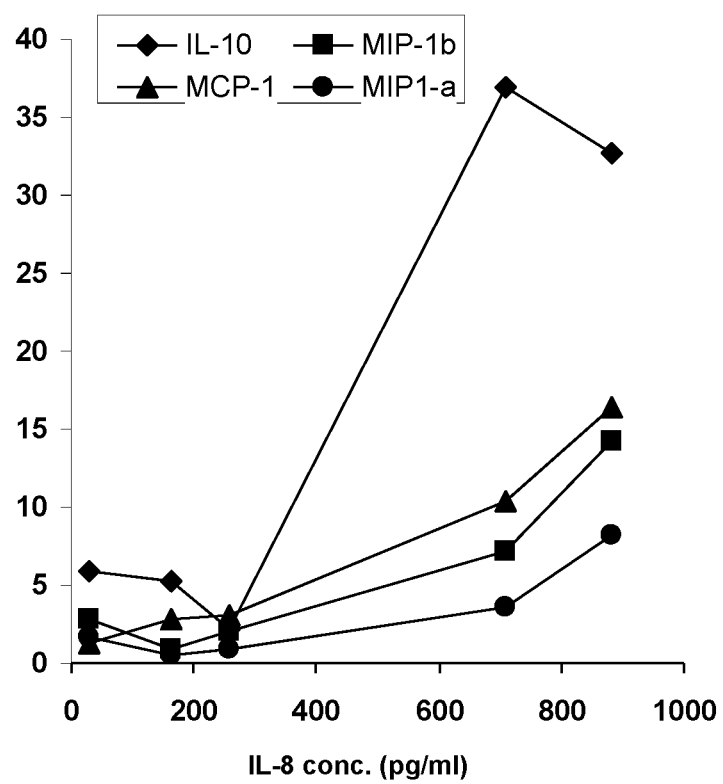

METHOD FOR DIAGNOSING AND TREATING FIBROMYALGIA

CROSS REFERENCE TO RELATED APPLICATIONS

This application is a continuation of U.S. patent application Ser. No. 14/692,338, filed Apr. 21, 2015, which is a continuation of U.S. patent application Ser. No. 14/444,779, filed Jul. 28, 2014 (now abandoned), which is a continuation of U.S. patent application Ser. No. 14/358,396, filed May 15, 2014 (now abandoned), which is the U.S. National Phase Application of PCT/US2011/55985, filed Oct. 12, 2011, which claims priority from U.S. Provisional Application No. 61/392,371, filed Oct. 12, 2010, the disclosure of each of which is incorporated by reference in their entireties.

BACKGROUND OF THE INVENTION

Fibromyalgia (FM) or FM syndrome is a medical disorder of unknown etiology characterized by chronic widespread joint and muscle pain. Other symptoms include allodynia (a heightened and painful response to pressure), debilitating fatigue, sleep disturbance, and joint stiffness, numbness, tingling and cognitive dysfunction. The etio-pathophysiology of FM is not completely understood, although the syndrome is currently viewed as a malfunctioning of the central nervous system resulting in amplification of widespread pain. In addition, genetic and environmental factors have been suggested to play a role in the etio-pathophysiology of FM.

Although FM is generally regarded as a non-inflammatory and non-autoimmune disease, some patients display autoimmunity features. FM has been found to be common in patients with autoimmune disorders, such as multiple sclerosis, systemic lupus erythematosus (SLE) (Middleton et al. (1994). Arthritis & Rheumatism 37, pp. 1181-1188; Morand, 1994), Sjogren Syndrome (Vitali, 1989; Tishler, 1997) and rheumatoid arthritis (Wolfe, 2004). The widespread pain and inflammation in the musculoskeletal system of FM patients suggest that the immune system may play a role in the etio-pathophysiology of FM. Consequently, studies have been carried out to map the cytokine levels in the serum of FM patients to determine if cytokines play a role in the etio-physiopathology of the disease. (Wallace, D. J., et al., Arthritis and Rheumatism 32:1334-135 (1989); Wallace, D. J., et al., Rheumatology 40:743-749 (2001); Togo, F. et al., Exp. Biol. Med. 234:232-240, (2009); Bazzichi, L. et al., Clin. & Exp. Rheumatol 25:225-230 (2007)). However, the results of these studies have been conflicting (Menzies and Lyon, Biol. Research for Nursing 11:387-394 (2010)) and to date, there is neither a system yet available for evaluating whether an individual with chronic widespread pain has FM or will develop FM, nor a systematic method or criteria for evaluating and diagnosing such individuals. Furthermore, there is no system available that is useful for distinguishing FM from the other autoimmune disorders, which are also characterized by chronic widespread pain.

Accordingly, there is a need for a system useful for diagnosing and evaluating FM to distinguish it from other autoimmune diseases and properly treat the disorder. The present invention addresses this and other needs.

SUMMARY OF THE INVENTION

The invention provides methods, kits and reagents for diagnosing fibromyalgia (FM) in an individual. In one embodiment, the present invention provides methods for diagnosing FM in an individual by determining whether the levels of one or more cytokines in the individual are altered. In one embodiment, determining whether the individual has altered levels of cytokines comprises comparing the individual's levels to control cytokine levels. In a further embodiment, control cytokine levels are determined from a database or derived from an individual who has not been diagnosed with FM. Altered level(s) of the cytokines measured in the affected individual compared to the level from the control level is predictive/indicative of FM in the individual.

In a further embodiment, the individual is diagnosed with FM if at least about half the cytokines tested have altered expression (i.e., are differentially expressed as compared to a control level). Cytokine expression is altered, in one embodiment, if it is expressed at levels at least about 1.5× higher or lower, as compared to cytokine expression at a control level. In one embodiment, a control level is determined by determining cytokine expression in a healthy patient, cell culture levels, or by looking up the value in a database.

In one embodiment, the cytokine expression levels are tested with the use of antibodies specific for the cytokines. In a further embodiment, the antibody assay is bead-based.

In various aspects, the invention involves determining the protein or mRNA levels of one or more of IL-5, IL-6, IL-8, IL-10, IFN-γ, MCP-1, MIP-α, MIP-β. In another aspect, the invention further includes determining the levels of one or more of IL-1RA, IL2R, IL-7, IL-12 (p40/p70), IL-13, IL-15, IL-17, IFN-α, IP-10, MIG, VEGF, G-CSF, EGF, FGF-basic and HGF. In yet another aspect, the invention also includes determining the levels of IL-9 and PDGF-BB or a combination thereof.

In one aspect, the invention provides methods for evaluating an individual at risk for developing FM by determining whether the levels of one or more; two or more; three or more; four or more; five or more; six or more; seven or more; eight or more; nine or more; or ten or more cytokines in the individual are altered. In a further embodiment, the cytokines are selected from two or more, or three or more, or four or more, or five or more of IL-1Rα, IL2R, IL-7, IL-12 (p40/p70), IL-13, IL-15, IL-17, IFN-α, IP-10, MIG, VEGF, G-CSF, EGF, FGF-basic and HGF.

In another aspect, the invention provides methods for distinguishing FM from other diseases characterized by widespread chronic pain, such as rheumatoid arthritis, SLE, Sjogren and multiple sclerosis. The method comprises determining the levels or patterns of expression of cytokines in individuals suspected of having FM, or individuals afflicted with FM or individuals at risk of developing FM, and comparing the levels to the cytokine levels of an individual with a disease of widespread pain. The difference or altered levels of expression or pattern of expression of one or more cytokines in individuals suspected to have FM compared to individuals diagnosed with a disease of widespread pain (e.g., rheumatoid arthritis, SLE, Sjogren, multiple sclerosis) provides a way to distinguish FM at the molecular level, from these other forms of debilitating immune disorders.

In yet another aspect, the invention provides methods for treating an individual diagnosed with FM. In even another aspect, the invention provides a method for determining the efficacy of the treatment in individuals diagnosed with FM. In certain aspects, the invention provides a method for determining the levels of or patterns of expression of cytokines in individuals afflicted with FM or are at risk of developing FM prior to, during or after administration of a small molecule or a biological factor to treat FM. The difference or altered levels or patterns of expression of cytokines in the individuals after treatment as compared to before treatment is indicative of the efficacy of the treatment.

In one aspect, the invention provides a kit for evaluating an individual afflicted with or at risk of developing FM. The kit of the invention may include one or more reagents for detecting cytokine, or a plurality of cytokines, a detection system and an instruction manual.

DESCRIPTION OF THE FIGURES

FIG. 1 is a graph showing the correlation of plasma IL-8 levels with a decrease in patient PBMC responses to PMA challenges. The ratios of mean cytokine concentrations in a control group to the patient cytokine levels in stimulated cultures were plotted against plasma IL-8 concentrations for patients whose IL-8 levels were above 20 pg/mL, two times the lower limit of detection.

DETAILED DESCRIPTION OF THE INVENTION

The present invention provides methods, kits and reagents for diagnosing fibromyalgia (FM) in an individual. In one embodiment, the present invention provides methods for diagnosing FM in an individual by determining the levels of one or more cytokines in the individual and comparing the levels of the one or more of the cytokines from the individuals to the levels of control samples, or determining whether the cytokine levels are altered in the individual. In one embodiment, cytokine levels are tested on the protein level. In another embodiment, cytokine levels are determined at the mRNA level. In yet another embodiment, both mRNA and protein levels for the cytokines are examined in the methods provided herein.

In one embodiment, the methods for diagnosing or predicting fibromyalgia in a patient involve determining or assaying the levels of at least one, at least two, at least three, at least four, at least five, at least six, at least seven, at least eight, at least nine, or at least ten or more cytokines in the plasma of blood samples obtained from individuals suspected of being afflicted with FM or at risk for FM. In a further embodiment, the method involves determining or assaying the levels of at least one, at least two, at least three, at least four, at least five, at least six, at least seven, at least eight, at least nine, or at least ten or more cytokines in the peripheral blood mononuclear cells (PBMCs) that have been separated from the plasma of blood samples obtained from the individuals. These levels are then analyzed to determine if the levels are altered. For example, the levels in the individual's sample, in one embodiment, are compared to levels in a control sample, for example, a sample known to not have FM. In one embodiment, a change in expression in a majority of the cytokines tested is determinative/indicative of the individual having FM. In another embodiment, a change in expression of at least about 33% or at least about 67% of the cytokines tested is determinative/indicative of a positive diagnosis of FM.

The blood or plasma sample tested may be stimulated or un-stimulated. That is, cell proliferation may be induced prior to assaying the cytokine levels. In one embodiment, the PBMCs are un-stimulated. In another embodiment, the PBMCs are stimulated to cause proliferation of the cells prior to assaying for cytokines. Methods for stimulating PBMCs are known in the art, and include, but are not limited to, the addition of mitogens to the cells. Non-limiting examples of mitogens include lipopolysaccharide (LPS), phytohemagglutinin (PHA), or phorbol ester, such as phorbol myristate acetate (PMA) with or without ionomycin, pokeweed mitogen (PWM), concavalin A (Con-A), or combinations thereof.

The term "cytokine" as used herein refers to small proteins that are secreted by specific cells of the immune system and glial cells, and include lymphokines, interleukins, and chemokines and their corresponding receptors, such as but not limited to IL-1, IL-2, IL-4, IL-5, IL-6, IL-7, IL-8, IL-10, IL-12, IL-13, IL-15, IL-17, IL-21, IFN-γ, IFN-α, TNF-α, IP-10, MCP-1, MIG, MIP-α, GM-CSF, Eotaxin, RANTES, etc. In another aspect, the invention further includes determining the levels of one or more of IL-1RA, IL2R, IL-7, IL-12 (p40/p70), IL-13, IL-15, IL-17, IFN-α, IP-10, MIG, VEGF, G-CSF, EGF, FGF-basic and HGF. In yet another aspect, the invention also includes determining the levels of IL-9 and PDGF-BB or a combination thereof. The cytokine may be inflammatory or anti-inflammatory. In one embodiment, the cytokine to be assayed may be a full length polypeptide, protein, a glycoprotein or a fragment thereof. Other proteins that can be assayed include hormones, heat-shock proteins, antibodies such as but not limited to anti-nuclear antibody (ANA), thyroid antibodies, anti-extractable nuclear antibodies (ENA), IgG subclasses, anti-nuclear factors (FAN), rheumatoid factor (RF), receptor proteins and ligands, etc. In other embodiment, the level of cytokine assayed maybe a mRNA, miRNA, or DNA.

The present invention is not limited by any particular combination of cytokines. For example, the expression levels of cytokines included in commercial cytokine panels (or cytokine subsets thereof) can be evaluated by the methods provided herein. Various combinations of cytokines for use in the present invention are provided in Table 1 below. Subsets of these combinations may also be used in the methods provided herein. It should be understood that these combinations are representative, and should not be construed as limiting the invention.

TABLE 1

Non-limiting cytokine panels for use with the present invention.

| Panel 1 | Panel 2 | Panel 3 | Panel 4 | Panel 5 |
|---|---|---|---|---|
| IL5 | IFN-γ | TranSignal Human Cytokine Antibody Array 3.0 (or a subset of cytokines provided in this assay) | Bio-Plex Pro magnetic Cytokine Assay (any of these assays may be used, i.e., the 8-plex, 17-plex, 21-plex, 27-plex | five or more chemokines |
| IL6 | IL-1β | | | |
| IL8 | IL-2 | | | |
| IL 10 | IL-4 | | | |
| IFN-γ | IL-5 | | | |
| MCP-1 | IL-6 | | | |
| MIP-α | IL-8 | | | |
| MIP-β | IL-10 | | | |
| | TNF-α | | | |
| | MIP-1β | | | |
| | MCP-1 | | | |
| | MIP-1α | | | |
| | Rantes | | | |

| Panel 6 | Panel 7 | Panel 8 | Panel 9 | Panel 10 |
|---|---|---|---|---|
| IL5 | IL-6 | IL-2 | IL-8 | IFN-γ |
| IL6 | IL-8 | IL-4 | IL-10 | IL-1β |
| IL8 | IL-10 | IL-5 | TNF-α | IL-2 |
| IL 10 | TNF-α | IL-6 | MIP-1β | |
| IFN-γ | MIP-1β | | MCP-1 | |
| | MCP-1 | | Rantes | |
| | MIP-1α | | | |

The present invention, in one embodiment, is directed to the diagnosis of fibromyalgia by determining whether the expression levels of one or more cytokines in an individual are altered. In one embodiment, the method comprises determining whether the levels of at least two, at least three, at least four, at least five, at least six, at least seven, at least eight, at least nine, at least ten, at least eleven, at least twelve or at least thirteen cytokines, or at least thirteen or more cytokines in an individual are altered. As discussed below, commercial assays are available to measure the expression of up to 27 cytokines in a sample. The methods provided herein are amenable for detection of this number of cytokines. In one embodiment, expression levels of a subset of the cytokines in a commercial assay are determined.

In one embodiment, to determine whether cytokine levels are altered, the cytokine levels in the individual are compared to control cytokine levels, for example, cytokine levels from a healthy patient, or cytokine levels reported for a patient without fibromyalgia (for example, levels reported in a database). In one embodiment, a positive diagnosis of fibromyalgia is provided if a majority of the cytokines tested have altered expression. In a further embodiment, a positive diagnosis of fibromyalgia is provided if at least about 67% of the cytokines tested have altered expression, or at least about 67% or more of the cytokines tested have altered expression. In a further embodiment, a positive diagnosis of fibromyalgia is provided if at least about 75%, or at least about 75% or more of the cytokines tested have altered expression. In even a further embodiment, a positive diagnosis of fibromyalgia is provided if the expression level of every cytokine tested, or about every cytokine tested in the patient is altered. In one embodiment, altered expression is determined by comparing the cytokine levels of the individual's sample to control levels. Control levels, in one embodiment, are determined by testing a sample of an individual known to not have FM. In another embodiment, control levels are known, for example, from a database.

In one embodiment, cytokine expression is measured at the mRNA level, for example, by quantitative RT-PCR (also known as real time RT-PCR). mRNA expression levels can also be measured by arrays. For example, multiplex quantitative RT-PCR, in one embodiment, is carried out to determine the mRNA expression levels of a cytokine panel. cytokine RT-PCR kits are commercially available, for example, from Roche.

In another embodiment, secreted cytokine levels are determined (i.e., at the protein level). In one embodiment, secreted cytokine levels are determined by using an antibody array, for example, the TranSignal Human Cytokine Antibody Array 3.0, available from Panomics. The Panomics array includes antibodies directed to the following cytokines: Apol/Fas, Leptin, Rantes, ICAM-1, IL-2, IL-7, CTLA, MIP1α, MIP1β, TGFβ, VCAM-1, IL-3, IL-8, IL-4, IL-10, IL-5, IL-12, IL-6, IL-15, IL-6R, IL-17, IL-1Rα, IL-1β, IL-1α, VEGF, IFNγ, TNFα, TNFRI, TNFRII, MIP-5, MIP4, MMP3, Eotaxin, GM-CSF, EGF, IP-10. In this embodiment, not all cytokines in the array need be probed for. For example, the expression levels of a subset of five cytokines, or five or more cytokines, or six cytokines, or six or more cytokines, or seven cytokines, or seven or more cytokines, or ten cytokines, or ten or more cytokines, or twelve cytokines, or twelve or more cytokines may be determined when carrying out the methods of the invention.

Secreted cytokine levels, in one embodiment, are determined with a multiplex immunoassay built on magnetic beads. For example, in one embodiment, the Bio-Plex Pro magnetic Cytokine Assay is used (Bio-Rad). In this embodiment, the Assay is commercially available as a ready to use kit, for example, for the detection of eight cytokines, seventeen cytokines, 21 cytokines or 27 cytokines. The full number or a subset of the cytokines may be detected in the methods of the invention. Alternatively, expression levels of cytokines can be tested in a sample by doing multiple assays on the sample, for example, in "singleplex" format. In one embodiment, the Bio-Rad singleplex cytokine assays are used.

Another antibody based bead assay is available from Invitrogen, and is also amenable to be used in the methods of the present invention. Specifically, the Human Cytokine Thirty-Plex antibody bead kit may be employed to detect the levels of a panel of cytokines in an individual. Although the assay can detect the levels of thirty cytokines, not all thirty need to be detected in order to carry out the methods provided herein. For example, as provided above, five, six, seven, eight, nine, ten, eleven or twelve cytokines can be assayed for their expression levels. The Invitrogen kit comprises analyte specific components for the measurement of human IL-1β, IL-1RA, IL-2, IL-2R, IL-4, IL-5, IL-6, IL-7, IL-8, IL-10, IL-12p40/p70, IL-13, IL-15, IL-17, TNF-α, IFN-α, IFN-γ, GM-CSF, MIP-1α, MIP-1β, IP-10, MIG, Eotaxin, RANTES, MCP-1, VEGF, G-CSF, EGF, FGF-basic, and HGF. These reagents, in one embodiment, are used in the Luminex® 100™ or 200™ System.

In one embodiment, if a majority of the cytokines assayed in the individual's sample have an altered expression level, or at least a majority of the cytokines have an altered expression level, or at least about a majority of the cytokines have an altered expression level, the individual is diagnosed with fibromyalgia. As provided above, altered cytokine levels can be determined by comparing the cytokine levels to control levels.

Methods for assaying cytokines at the protein or mRNA levels are well known in the art. Besides the assays provided above, other non-limiting examples of methods for assaying cytokines at the protein level include enzyme-linked immunoassay (ELISA), Tetramer assay, ELISPOT assay, Fluorospot assay, etc. The cytokines concentration in the plasma, culture supernatant, or cell lysate derived from PBMC can be measured, for example, by multiplex immunoassay based on Luminex xMAP bead array technology, or Bio-Plex 200 fluorescence bead reader (BioRad Laboratories, Hercules, Calif.). In one embodiment, the level of one or more cytokine mRNA can be detected (measured) by real time PCR, RT-PCR, Northern blot assay, array hybridization, sequencing, etc. The altered level(s) of the cytokines measured in the affected individual compared to the level from control group is predictive/indicative of FM in the individual. The cytokine levels in an individual with FM, for example, cytokine levels in a FM patient's blood, in one embodiment, are higher than the cytokine levels of a healthy patient, for each cytokine tested. In another embodiment, the cytokine levels in a FM patient's blood are lower than the cytokine levels of a healthy patient, for each cytokine tested. In yet another embodiment, the cytokine levels measured in a patient with FM may be higher or lower, depending on the panel of cytokines measured in the individual.

In the methods provided herein, in one embodiment, the expression levels of a panel of cytokines are determined. In one embodiment, a positive diagnosis of fibromyalgia is given if the expression levels (either mRNA or protein) of at least about 33% of the cytokines are altered in the individual. In another embodiment, a positive diagnosis of fibromyalgia is given if the expression levels (either mRNA or protein) of at least about 50% of the cytokines are altered in the individual. In another embodiment, a positive diagnosis of fibromyalgia is provided if the expression levels (either mRNA or protein) of at least about 67% of the cytokines are altered in the individual. In another embodiment, a positive diagnosis of fibromyalgia is given if the expression levels (either mRNA or protein) of at least about 75% of the cytokines are altered in the individual, or expression levels of at least about 75% or more of the cytokines are altered in the individual. For each cytokine, the altered expression can be an increase in expression or a decrease in expression. Additionally, each cytokine differentially expressed (i.e., the cytokines determined to have altered expression) need not be differentially expressed at the same level. Therefore, when examining expression of a panel of cytokines in an individual with fibromyalgia, one or more cytokines may have increased expression, while one or more cytokines may have a decrease in expression, and the differentially expressed cytokines may be differentially expressed at different levels. In one embodiment, altered expression is determined by comparing the cytokine levels of the individual's sample to control levels. Control levels, in one embodiment, are determined by determining cytokine levels in a sample of an individual known to not have FM. In another embodiment, control levels are known, for example, from a database.

Cytokine expression is "altered", or a cytokine is "differentially expressed", in an individual, in one embodiment, if expression of the cytokine in the individual's sample is at least about 1.5 times higher or lower than the expression of the same cytokine at a control level. In another embodiment, cytokine expression is "altered" if cytokine expression in the individual's sample is at least about 2 times higher or lower than the expression of the same cytokine at a control or baseline level (i.e., levels reported for a healthy patient). In another embodiment, cytokine expression is "altered" if cytokine expression in the individual is at least about 2.5 times higher or lower (or at least about 2.5 times or more higher or lower) than the control expression level of the same cytokine. In yet another embodiment, cytokine expression is "altered" if cytokine expression in the individual is at least about 3 times higher or lower (or at least about 3 times or more higher or lower) than the control expression level of the same cytokine. In another embodiment, cytokine expression is "altered" if cytokine expression in the individual is at least about 5 times higher or lower (or at least about 5 times or more higher or lower) than the control expression level of the same cytokine. In even another embodiment, cytokine expression is "altered" if cytokine expression in the individual is at least about 10 times higher or lower than the control expression level of the same cytokine in a control sample. In yet another embodiment, cytokine expression is altered if cytokine expression in the individual is at least about 10 times or more, higher or lower, than the control expression level of the same cytokine. As provided above, control expression level may be determined from values in a database, from a non-FM sample or individual.

Altered expression of the cytokine may be the same or different for each individual cytokine that is differentially expressed. For example, the expression of one cytokine (mRNA or protein) may be 2× lower, or about 2× lower, than the expression of the same cytokine in a control sample, while the expression of a second cytokine may be 1.5× lower, or about 1.5× lower, than the expression of the same cytokine in a control sample. As discussed above, altered expression includes both higher and lower expression of the cytokine, compared to a control level.

The control level may be determined from a control group. In one embodiment, the control group may be healthy individuals in a population, where the individuals do not exhibit chronic pain. The altered level of cytokines can be determined using an algorithm and the raw data obtained by measuring the levels of cytokines which have been stored in a computer system, or any other medium that is linked to a computer or machine. In one aspect, the method further includes evaluation of the individual's clinical and physical symptoms in conjunction with determining the levels of one or more cytokines. For example, the method includes evaluation of tender points in the individual. The pain threshold is calculated and assigned a score on a subjective basis. The scores derived from the assessment of the clinical and physical symptoms may be included in the statistical analysis for the cytokines. In a further embodiment, the method includes determining the levels of various factors or markers, such as but not limited to Rheumatoid Factor (RF), or a specific marker of inflammation such as the erythrocyte sedimentation rate (ESR).

In one embodiment, the individual subject to the methods of the invention is at risk for developing FM. The cytokine levels of these individuals are determined and compared to control levels. As discussed above, levels of one or more; two or more; three or more; four or more; five or more; six or more; seven or more; eight or more; nine or more; or ten or more cytokines may be determined. Altered expression of at least a portion of the cytokines (e.g., a majority of the cytokines, or at least about 33% of the cytokines tested, or at least about 25% of the cytokines tested, or at least about 50% or more of the cytokines tested) is indicative of FM, and the individual is therefore diagnosed with FM.

In one embodiment, the method comprises determining whether the cytokine levels in the individual are altered. In a further embodiment, the determining step is carried out by comparing the levels of the cytokines in the individual to those of a control sample, and determining whether cytokine expression is altered. In one embodiment, altered expression of at least about 33% (or at least 33% or more) of the cytokines tested is indicative of FM, and the individual is therefore diagnosed with FM. In one embodiment, altered expression of at least about 25% of the cytokines tested is indicative of FM, and the individual is therefore diagnosed with FM. In one embodiment, altered expression of at least about 20% of the cytokines tested is indicative of FM, and the individual is therefore diagnosed with FM.

Altered expression, in one embodiment, is a difference in cytokine expression of at least about 1.5×, at least about 2×, at least about 2.5×, at least about 3×, at least about 4×, at least about 5×, at least about 10×, or at least about 10× or more, in the individual, compared to control levels. The difference may be an increase or decrease in expression.

In one embodiment, an individual may be at risk for developing FM if the individual experienced or expressed symptoms that are characterized by chronic widespread pain in the muscle and connective tissue, a heightened and painful response to pressure. The pain may last for more than 3 months and may affect all four quadrants of the body. (The American College of Rheumatology). Other symptoms may include debilitating fatigue, sleep disturbance, joint stiffness, numbness and tingling and cognitive dysfunction. Further, individuals with known family members diagnosed with FM may also be at risk for FM. In another embodiment, an individual may be at risk for developing FM if the individual carries one or more mutation in the gene(s) that affect the inflammatory pathway. For example, mutations in the MEFV gene, which lead to Familiar Mediterranean Fever (FMF) have been suggested to be responsible for symptoms of fever and muscle aches. Feng et al. (PLos One 4:e8480 (2009)) reported that patients heterozygous for rare missense variants of the MEFV gene may be predisposed to FMS.

In another aspect, the invention provides methods for distinguishing FM from other diseases characterized by widespread chronic pain. Because individuals afflicted with FM or are at risk for developing FM exhibit widespread chronic pain that is also characteristic of individuals afflicted or at risk of developing inflammatory or autoimmune diseases such as rheumatoid arthritis, SLE, etc., a method or system for distinguishing FM from these diseases would not only be beneficial to the patient in providing a proper treatment or standard of care relevant to the disease but would also beneficial in that it assist in eliminating higher cost of health care, particularly in the use of unnecessary medications that not only do not alleviate the symptoms but may result in further exacerbation of the disease.

The present invention provides a method for distinguishing FM from other diseases characterized by widespread chronic pain by determining the levels of one or more; two or more; three or more; four or more; five or more; six or more; seven or more; eight or more; nine or more; or ten or more cytokines in the individual. The altered levels and or patterns of expression of one or more of the cytokines measured in the individual afflicted with FM or at risk for developing FM are compared to the levels or patterns of expression of cytokines in individuals diagnosed with, for example, rheumatoid arthritis, etc, are useful for predicting that the individual is likely to have FM. The method comprises comparing the levels of the cytokines in the individual with FM or at risk for FM to those of an individual with another disease characterized by widespread chronic pain (e.g., rheumatoid arthritis), and determining whether cytokine expression is altered. Altered expression, in one embodiment, is a difference in cytokine expression of at least about 1.5×, at least about 2×, at least about 2.5×, at least about 3×, at least about 5× or at least about 10× or more in the individual, compared to control levels.

In another aspect, the invention provides methods for treating an individual diagnosed with FM. In another aspect, the invention provides methods for evaluating the efficacy of treatment in an individual diagnosed with FM. For example, the method involves determining as a baseline the level of cytokine expressed in the individual diagnosed with FM prior to treatment. Following treatment, subsequent measurements of cytokine levels are carried out to determine the levels or patterns of expression of cytokines. The altered levels and or patterns of expression of one or more of the cytokines measured in the individual afflicted with FM or at risk for developing FM and undergoing treatment are compared to the levels or patterns of expression of cytokines before treatment.

In yet another aspect of the invention, the invention provides a kit for evaluating an individual afflicted with or at risk of developing FM. The invention provides a kit which includes a multiplex of reagents for determining one or more cytokines. In one embodiment, the kit includes a multiplex of antibody-coupled beads, each antibody being specific for each of the cytokines to be determined in the assay such as but not limited to ELISA, tetramer assay, ELISPOT, Fluor-spot, immuno-diffusion etc. The kit also provides a detection system. Non-limiting examples of detection systems include one or more radio-labeled, fluorescent-labeled, enzyme-labeled secondary antibody or antibodies. Examples of fluorescent-labels are well known in the art and they include fluorescein, Texas red, rhodamine, etc. The bound sample can be analyzed using a flow cytometer, a fluorescent microscope, a ELISA reader, Luminex xMAP bead array technology, or Bio-Plex 200 fluorescence bead reader.

EXAMPLES

Isolation of Peripheral Blood Mononuclear Cells (PBMC)

Twenty-30 mL of blood were withdrawn in 7-mL tubes containing 0.081 mL of 15% K3-EDTA solution (BD Vacutainer®, BD, Franklin Lakes, N.J.) by venipuncture from patients and healthy volunteers after obtaining the consent for research. Blood was transferred to 50-mL tubes and diluted 1:1 in GIBCO® Hank's balanced salt solution (HBSS, Invitrogen, Carlsbad, Calif.). The resulting solution was layered on top of 15 mL Ficoll (Histopaque-1077, Sigma-Aldrich, St. Louis, Mo.) in 50-mL tubes and centrifuged at 1800 rpm for 20 minutes. The top layer was aspirated and discarded and the interphase containing PMBC was harvested and transferred into a new 50-mL tube. The tube was filled with HBSS and the contents were mixed by gentle rocking. Cells were collected by centrifugation at 2000 rpm for 10 minutes and resuspended in 10 mL complete RPMI-1640 medium supplemented with 10% fetal bovine serum, 1% penicillin-streptomycin mixture and 1% L-glutamine solution (Invitrogen, Carlsbad, Calif.). Cell viability and count was determined using Trypan blue exclusion assay.

Culture of PBMC

Cells were suspended at a concentration $10^6$ cells/mL in a complete RPMI medium. Three mL suspension was placed in tissue culture dishes (Nalge Nunc International, Rochester, N.Y.) and 10 µg/mL PHA-P (Sigma-Aldrich®, St. Louis, Mo.) as well as the mixture of 1 µg/mL phorbol-12-myristate-13-acetate (PMA) and 1 µg/mL ionomycin (EMD Biosciences, Inc, Darmstadt, Germany) were added into the separate dishes. Triplicate plates were used for each challenge. No mitogens were added to three plates which served as a control for basal levels of expression. Plates were placed in the $CO_2$ water jacketed incubator (Forma Scientific, Marjetta, OH) and incubated for 18 hours.

Cytokine Assay

After overnight culture of PBMCs in the media alone or in the presence of mitogens, 1 mL supernatant was removed from each plate, centrifuged at 16,000 g at +4° C., for 10 minutes and clear cell-free culture media were collected, placed in the new 1.7-mL tube and kept frozen at −80° C.

Cytokine and chemokine concentrations in plasma as well as in culture supernatants were measured by multiplex immunoassay based on Luminex xMAP™ bead array technology and Bio-Plex 200 fluorescence bead reader (BioRad Laboratories, Hercules, Calif.). Three panels of antibody-conjugated beads for measuring human inflammatory cytokines (GM-CSF, IL-1β, IL-6, IL-8, TNF-α), Th1/Th2 cytokines (IFN-γ, IL-2, IL-4, IL-5, IL-10) and chemokines (MIP-1α, MIP-1β, MCP-1, Eotaxin, RANTES) (BioSource, Camarillo, Calif.) were used in the assay according to the manufacturer instructions. Other panels that can be included are IL-1RA, IL-2R, IL-7, IL-12 (p40/p70), IL-13, IL-15, IL-17, IFN-, IP-10, MIG, VEGF, EGF, FGF-basic, and HGF (InVitrogen) or IL-1RA, IL-7, IL-9, IL-12, IL13, IL-15, IL-17, FGF-basic, G-CSF, IP-10, VEGF, PDGF-BB (Bio-Rad)

Concentration values were transferred to Microsoft Office Excel 2003 software (Microsoft Corporation, Redmond, Wash.) and means as well as standard deviations were calculated for each cytokine concentration. Cytokine concentrations in patients were compared to those of healthy individuals by using Student's t-test. The confidence level was set at 5%.

Results

Concentration of Cytokines in Plasma of FM Patients.

Concentrations of 15 cytokines, GM-CSF, IFN-γ, IL-1β, IL-2, IL-4, IL-5, IL-6, IL-8, IL-10, TNF-α, MIP-1β, MCP-1, Eotaxin, MIP1-a and Rantes was measured in plasma of seventeen FM patients and fifteen control subjects. The results is shown in Table 2 below.

TABLE 2

Concentrations of Cytokines in Plasma

| Cytokine/Chemokine | Mean Controls (pg/ml) | Mean Patients (pg/ml) | Patient/Control Ratio |
|---|---|---|---|
| GM-CSF | 52.0 ± 58.5 | 61.1 ± 60.2 | 1.2 |
| IFN-γ | 21.7 ± 18.3 | 37.8 ± 30.4 | 1.7 |
| IL-1β | 52.4 ± 68.1 | 45.0 ± 12.8 | 0.9 |
| IL-2 | 8.6 ± 11.5 | 5.5 ± 10.6 | 1.3 |
| IL-4 | 17.4 ± 13.9 | 34.2 ± 14.8 | 2.0 |
| IL-5 | 9.1 ± 8.0 | 21.4 ± 7.3 | 2.4 |
| IL-6 | 7.7 ± 4.5 | 18.2 ± 8.5 | 2.4* |
| IL-8 | 24.8 ± 8.2 | 260.5 ± 345.5 | 10.5* |
| IL-10 | 12.0 ± 9.7 | 13.9 ± 10.9 | 1.2 |
| TNF-α | 9.3 ± 7.7 | 15.2 ± 4.8 | 1.6 |
| MIP-1β | 633.4 ± 1706.8 | 181.1 ± 160.3 | 0.3 |
| MCP-1 | 531.6 ± 659.8 | 407.1 ± 318.6 | 0.8 |
| Eotaxin | 252.0 ± 260.5 | 228.9 ± 217.5 | 0.9 |
| MIP-1α | 157.0 ± 123.5 | 146.1 ± 129.9 | 0.9 |
| Rantes | 7033.1 ± 6913.6 | 7332.6 ± 7256.6 | 1.0 |

Statistically significant changes are marked by *

As shown in Table 2 above, when cytokine levels in FM samples were compared with the control values, no statistically significant difference were observed for most cytokines with the exception of IL-6 and IL-8. A 2.4 fold increase in IL-6 levels and a 10.5 fold increase in IL-8 concentrations in patient samples were observed.

Concentration of Cytokines in Activated PBMC Cultures.

To determine if cytokine production by immune cells is altered in FM patients, we determined the cellular responses to mitogenic activators phytohemagglutinin (PHA) and Phorbol-12-myristate-13-acetate (PMA) in combination with ionomycin. PHA, a lectin from *Phaseolus vulgaris* (red kidney bean), induces PBMC proliferation as well as the secretion of cytokines [Leavitt, 1977; Yachnin, 1972]. PMA and ionomycin also stimulate all types of cells found in PBMC and activate extracellular expression of cytokines [Kurtzhals, 1995; Tsuchida, 1988; Jason, 1997]. We therefore cultured PBMC isolated from blood samples from seventeen patients and seventeen control subjects in the presence of either PHA or PMA/ionomycin and determined concentrations of 15 cytokines in culture supernatants.

TABLE 3

Concentrations of Cytokines in Stimulated PBMC Cultures

| | Media | | PHA | | | PMA/ionomycin | | |
|---|---|---|---|---|---|---|---|---|
| Cytokine | Controls | Patients | Controls | Patients | Ratio | Controls | Patients | Ratio |
| GM-CSF | 22 ± 12 | 52 ± 43 | 276 ± 209 | 263 ± 225 | 1.0 | 952 ± 1365 | 314 ± 320 | 3.0* |
| IFN-γ | OOR< | OOR< | 95 ± 142 | 81 ± 105 | 1.2 | 5295 ± 9415 | 1069 ± 1429 | 4.9* |
| IL-1β | 11.1 ± 4.5 | 17.5 ± 6.3 | 326 ± 317 | 208 ± 373 | 1.6 | 84 ± 83 | 61 ± 98 | 1.4 |
| IL-2 | OOR< | OOR< | 301 ± 268 | 179 ± 167 | 1.7 | 20105 ± 21706 | 8946 ± 7996 | 2.2* |
| IL-4 | OOR< | OOR< | 89 ± 106 | 38 ± 54 | 2.3 | 396 ± 629 | 119 ± 147 | 3.3 |
| IL-5 | OOR< | OOR< | 14 ± 10 | 5.1 ± 5.3 | 2.8* | 144 ± 220 | 31 ± 20 | 4.6* |
| IL-6 | 9.8 ± 11.7 | 8.5 ± 7.3 | 5512 ± 5507 | 3856 ± 4821 | 1.4 | 999 ± 2345 | 158 ± 149 | 6.3 |
| IL-8 | 1178 ± 1505 | 1488 ± 1599 | 97549 ± 85565 | 76122 ± 62691 | 1.3 | 37951 ± 41929 | 21701 ± 18007 | 1.7 |
| IL-10 | OOR< | OOR< | 179 ± 167 | 48 ± 42 | 3.7* | 461 ± 904 | 56 ± 50 | 8.2* |
| TNF-α | 1.8 ± 1.5 | 7.5 ± 1.8 | 1287 ± 2780 | 1226 ± 1965 | 1.0 | 2316 ± 3887 | 1186 ± 1823 | 2.0 |
| MIP-1β | 81 ± 88 | 55 ± 44 | 10667 ± 8884 | 5112 ± 4094 | 2.1* | 21507 ± 31514 | 3244 ± 2546 | 6.6* |
| MCP-1 | 319 ± 235 | 436 ± 451 | 28842 ± 26583 | 12319 ± 13007 | 2.3* | 1312 ± 1956 | 859 ± 937 | 1.5 |
| MIP-1α | 58 ± 51 | 41 ± 32 | 9033 ± 7332 | 5290 ± 4655 | 1.7* | 9600 ± 14226 | 2363 ± 2103 | 4.1* |
| Rantes | 733 ± 11826 | 712 ± 1304 | 2987 ± 3893 | 1313 ± 1475 | 2.3 | 8609 ± 15542 | 2404 ± 2511 | 3.6 |

Statistically significant changes are marked by *

As shown in Table 3, unstimulated PBMC cultures produced low levels of cytokines. In contrast, in both PHA and PMA/ionomycin challenges, extracellular expression of all cytokines tested was significantly activated with the exception of Eotaxin (not shown), resulting in an increased cytokine concentrations in culture supernatants. When cytokine levels in patient samples were compared to the control values, the concentrations of most cytokines were lower in FM samples (compare to Table 2). The decrease was statistically significant for cytokines IL-5, IL-10, MIP-1β, MCP-1 and MIP-1α in PHA challenges and for cytokines GM-CSF, IFN-γ, IL-2, IL-5, IL-10, MIP-1β and MIP-1α in PMA/ionomycin challenges.

Correlation of Plasma IL-8 Levels with a Decreased PBMC Activity in FM Patients.

A number of reports observed an increase in the levels of proinflammatory cytokine IL-8 in sera of FM patients [Wallace, et al., Rheumatol. 40:743-749, (2001); Gur, et al., J. Rheumatol. 29:358-361, (2002); Gur, 2002] which correlates well with clinical manifestations [Bazzichi et al., Clin. Exp. Rheumatol. 25:225-230, (2007); Wang, 2008; Wang, 2009]. A significant increase in plasma IL-8 levels in the group of patient compared to the controls was also observed (Table 2). At the same time, the activity of immune cells stimulated with mitogens was decreased (Table 3). To determine if a decrease in PBMC activity in patients correlates with the plasma IL-8 levels PBMC cytokine responses were compared to mitogen challenges with IL-8 concentrations in plasma. Only cytokines which were decreased by a statistically significant value in either PHA or PMA/ionomycin challenge were analyzed. We observed a significant correlation of a decrease in cytokine responses to PHA challenges with plasma IL-8 levels for all analyzed cytokines (FIG. 1). The correlation was most pronounced at IL-8 concentrations above 300 pg/mL. A decrease in cytokine responses to PMA/ionomycin challenge did not correlate with plasma IL-8 levels (not shown).

By identifying abnormalities in the cytokine expression pattern associated with FM we will be able to evaluate patients with FM-like symptoms which will lead to more accurate FM diagnoses. Development of diagnostic kits based on measuring cytokine expression will also make it possible to evaluate the efficacy of different treatment options which will result in more effective therapies. Once a clear link between particular cytokines and a disease is established then various modalities of treatment to neutralize or suppress the cytokines might be developed as a treatment.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

All publications, patents and patent applications herein are incorporated by reference to the same extent as if each individual publication or patent application was specifically and individually indicated to be incorporated by reference. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, the foregoing description has been given for clearness of understanding only and no unnecessary limitations should be understood therefrom. It will be understood that the description is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating fibromyalgia (FM) in an individual, the method comprising:
    (a) stimulating a peripheral blood mononuclear cell (PBMC) sample obtained from an individual previously diagnosed with FM with one or more mitogens;
    (b) determining expression levels in the PBMC sample of at least four cytokines selected from the group consisting of interleukin 5 (IL5), interleukin 6 (IL6), interleukin 8 (IL8), interleukin 10 (IL 10), interferon-γ (IFN-γ), monocyte chemotactic protein 1 (MCP-1), macrophage inflammatory protein-1α (MIP-1α) and macrophage inflammatory protein-1β (MIP-1β) at the protein level by an antibody bead-based capture assay, wherein the bead-based capture assay comprises beads derivatized with antibodies specific to the at least four cytokines;
    (c) comparing the determined levels of protein expression to the expression levels of the at least four cytokines in a control sample;
    (d) identifying the individual as having the at least four cytokines expression levels decreased by at least about 1.5 times in the PBMC sample obtained from the individual previously diagnosed with FM as compared to the expression levels of the control sample; and
    (e) administering to the identified individual an effective amount of a FM standard of care selected from the group consisting of duloxetine, pregabalin, gabapentin and milnacipran.

2. The method of claim 1, wherein determining the protein expression levels in the PBMC sample comprises determining the protein expression levels of at least five cytokines selected from the group consisting of IL5, IL6, IL8, IL 10, IFN-γ, MCP-1, MIP-1α and MIP-1β.

3. The method of claim 1, wherein determining the protein expression levels in the PBMC sample comprises determining the protein expression levels of at least six cytokines selected from the group consisting of IL5, IL6, IL8, IL 10, IFN-γ, MCP-1, MIP-1α and MIP-1β.

4. The method of claim 1, wherein determining the protein expression levels in the PBMC sample comprises determining the protein expression levels of at least seven cytokines selected from the group consisting of IL5, IL6, IL8, IL 10, IFN-γ, MCP-1, MIP-1α and MIP-1β.

5. The method of claim 1, wherein determining the protein expression levels in the PBMC sample comprises determining the protein expression levels of IL5, IL6, IL8, IL 10, IFN-γ, MCP-1, MIP-1α and MIP-1β.

6. The method of claim 1, wherein the at least four cytokines are IL6, IL8, MIP-1α and MIP-1β.

7. The method of claim 1, wherein the one or more mitogens is selected from a T-cell mitogen, lipopolysaccharide (LPS), phorbol ester, phorbol myristate acetate (PMA) and PMA plus ionomycin.

8. The method of claim 7, wherein the T cell mitogen is selected from phytohemagglutinin (PHA), pokeweed mitogen (PWM) and concavalin A (Con-A).

9. The method of claim 1, wherein the decreased expression levels are characterized by a decrease in expression level of each of the at least four cytokines by at least about 2 times, at least about 2.5 times, at least about 3 times, at least about 4 times or at least about 5 times.

10. The method of claim 1, wherein the bead-based assay is a fluorescence-based assay.

11. The method of claim 1, wherein the bead-based capture assay is an enzyme-linked immunoassay (ELISA) assay.

12. The method of claim 1, wherein the beads derivatized with antibodies specific to the at least four cytokines are magnetic beads.

13. The method of claim 2, wherein the at least five cytokines comprise IL6, IL8, MIP-1α and MIP-1β and one or more cytokines selected from IL5, IL10, IFN-γ and MCP-1.

14. The method of claim 3, wherein the at least six cytokines comprise IL6, IL8, MIP-1α and MIP-1β and two or more cytokines selected from IL5, IL10, IFN-γ and MCP-1.

15. The method of claim 4, wherein the at least seven cytokines comprise IL6, IL8, MIP-1α and MIP-1β and three or more cytokines selected from IL5, IL10, IFN-γ and MCP-1.

16. The method of claim 1, wherein the control sample is obtained from an individual known not to have fibromyalgia.

17. The method of claim 1, wherein the control sample is obtained from an individual diagnosed with a disease of widespread pain selected from the group consisting of rheumatoid arthritis, systemic lupus erythematosus (SLE), Sjogren Syndrome and multiple sclerosis.

* * * * *